US012577194B2

(12) United States Patent
Sandbrink et al.

(10) Patent No.: US 12,577,194 B2
(45) Date of Patent: Mar. 17, 2026

(54) METHOD FOR THE HYDROGENATION OF AROMATIC NITRO COMPOUNDS

(71) Applicants: Covestro Deutschland AG, Leverkusen (DE); Covestro Intellectual Property GmbH & Co. KG, Leverkusen (DE); Lanxess Deutschland GmbH, Cologne (DE)

(72) Inventors: Lennart Sandbrink, Langenfeld (DE); Bernd Pennemann, Bergisch Gladbach (DE); Eberhard Zirngiebl, Cologne (DE); Martina Gerdinand, Bergisch Gladbach (DE); Hans-Jürgen Quella, Leverkusen (DE); Daniel Ullrich, Monheim am Rhein (DE); Marc Williams, Cologne (DE)

(73) Assignees: Covestro Deutschland AG, Leverkusen (DE); Lanxess Deutschland GmbH, Cologne (DE)

( * ) Notice: Subject to any disclaimer, the term of this patent is extended or adjusted under 35 U.S.C. 154(b) by 491 days.

(21) Appl. No.: 17/637,173

(22) PCT Filed: Aug. 27, 2020

(86) PCT No.: PCT/EP2020/073991
§ 371 (c)(1),
(2) Date: Feb. 22, 2022

(87) PCT Pub. No.: WO2021/037990
PCT Pub. Date: Mar. 4, 2021

(65) Prior Publication Data

US 2022/0289662 A1 Sep. 15, 2022

(30) Foreign Application Priority Data

Aug. 30, 2019 (EP) .................................... 19194563
Jun. 10, 2020 (EP) .................................... 20179290

(51) Int. Cl.
*C07C 209/36* (2006.01)
*B01J 23/72* (2006.01)
*B01J 37/02* (2006.01)
*B01J 37/08* (2006.01)

(52) U.S. Cl.
CPC ............. *C07C 209/36* (2013.01); *B01J 23/72* (2013.01); *B01J 37/0201* (2013.01); *B01J 37/08* (2013.01)

(58) Field of Classification Search
CPC ...... C07C 209/36; B01J 23/72; B01J 37/0201
See application file for complete search history.

(56) References Cited

U.S. PATENT DOCUMENTS 1,207,802 A 12/1916 Schmidt
2,891,094 A * 6/1959 Karkalits, Jr. ........... B01J 23/72 502/244
3,136,818 A 6/1964 Sperber et al.
3,224,981 A 12/1965 Stephens et al.
3,756,964 A 9/1973 Frazee et al.
3,803,010 A * 4/1974 Seaman ................. B01J 37/341 204/157.44
3,850,232 A 11/1974 Wanka et al.
3,871,445 A 3/1975 Wanka et al.
3,900,504 A 8/1975 Woerner
4,265,834 A 5/1981 Birkenstock et al.
5,808,157 A 9/1998 Langer et al.
5,877,350 A 3/1999 Langer et al.
5,968,869 A 10/1999 Nicolau et al.
6,043,394 A 3/2000 Langer et al.
6,080,890 A 6/2000 Langer et al.
6,107,514 A 8/2000 Nicolau et al.
6,201,160 B1 3/2001 Brudermüller et al.
6,262,307 B1 7/2001 Freund et al.
6,777,451 B2 8/2004 Koveal et al.
6,932,950 B1 8/2005 Guetlhuber (Continued)

FOREIGN PATENT DOCUMENTS

DE 3933661 A1 4/1991
DE 202006014116 U1 1/2007

(Continued)

OTHER PUBLICATIONS

Kislev—1964 (Year: 1964).*
Dust—Oxford English Dictionary (1989) (Year: 1989).*
J. Sun, et al, 4(12) Science advances, eaau3275, (2018)("Sun") (Year: 2018).*
The Fuji Silysia Chemical Ltd for CariACT-Q (2013)("Fuji") (Year: 2013).*
International Search Report, PCT/EP2020/073991, date of mailing: Oct. 22, 2020, Authorized officer: Wolfgang Fitz.

(Continued)

*Primary Examiner* — Alexander R Pagano
*Assistant Examiner* — Frank S. Hou
(74) *Attorney, Agent, or Firm* — Donald R. Palladino

(57) ABSTRACT

The present invention relates to a process for the preparation of an aromatic amine by hydrogenation of an aromatic nitro compound, comprising the following steps: (I) providing a copper tetramine salt-based impregnation catalyst, in particular an impregnation catalyst obtainable by the incipient wetness method, comprising a metal or metal oxide on a support as a hydrogenation catalyst. At least metallic or oxidic copper (in particular CuO) is present and the mole fraction of Cu based on all metals present is in the range of 075 to 1, and wherein the support comprises shaped silicon-dioxide shaped bodies or silicon-carbide shaped bodies; (II) optionally, activating the hydrogenation catalyst by treating with hydrogen in the absence of the aromatic nitro compound; and (III) reacting the aromatic nitro compound with hydrogen in the presence of the, optionally activated, hydrogenation catalyst to obtain the aromatic amine.

16 Claims, No Drawings

(56) References Cited

U.S. PATENT DOCUMENTS

| | | | |
|---|---|---|---|
| 7,449,037 | B2 | 11/2008 | Lehr et al. |
| 7,521,029 | B2 | 4/2009 | Guetlhuber et al. |
| 7,851,221 | B2 | 12/2010 | Garton et al. |
| 8,809,588 | B2 | 8/2014 | Konigsmann et al. |
| 9,067,864 | B2 | 6/2015 | Sommer et al. |
| 9,266,094 | B2 | 2/2016 | Merkel et al. |
| 2007/0036697 | A1 | 2/2007 | Gutlhuber et al. |
| 2011/0060169 | A1 | 3/2011 | Kaizik et al. |
| 2012/0065431 | A1 | 3/2012 | Koenigsmann et al. |
| 2018/0126361 | A1* | 5/2018 | Klasovsky ........... B01J 37/0203 |
| 2024/0157343 | A1* | 5/2024 | Pennemann ............. B01J 35/55 |

FOREIGN PATENT DOCUMENTS

| | | | |
|---|---|---|---|
| DE | 102010029924 | A1 | 12/2011 |
| EP | 1586370 | A2 | 10/2005 |
| GB | 823026 | A | 11/1959 |
| GB | 825602 | A | 12/1959 |
| JP | H0597780 | A | 4/1993 |
| WO | 20030022418 | A1 | 3/2003 |
| WO | 20040052524 | A1 | 6/2004 |

OTHER PUBLICATIONS

Carlo Perego et al., "Catalyst preparation methods" Catalysis Today 34 (1997) p. 281-305, Politenico di Milano, Milano, Italy.

D.L. Bernard et al., "X Radiation from Van de Graaff Accelerator Ion Sources". IEEE Transactions on Nuclear Science, PAC 1967, p. 181-186, University of Virginia, Jun. 1967.

Hagen, Chapter 14 Catalysis Reactors, "Industrial Catalysis", Wiley-VCH Verlag GmbH & Co. KGaA, Weinheim, Germany 2006.

Ruppel et al., "Catalytic Fixed-Bed Reactors", Ullmann's Encyclopedia of Industrial Chemistry, Wiley-VCH Verlag GmbH & Co. KGaA, Weinheim, Germany 2012.

Deutschmann et al., "Heterogeneous Catalysis and Solid Catalysts", Ullmann's Encyclopedia of Industrial Chemistry, Wiley-VCH GmbH & Co. KGaA, Weinheim Germany 2009.

Andrigo et al., "Fixed bed reactors", Catalysis Today 52, pp. 197-221, EniChem, Corporate Research Centre, Via Fauser 4, Elsevier Science B.V. Novara, Italy 1999.

Hartinger, Handbuch Abwasser und Recyclingtechnik [Handbook of Wastewater and Recycling Technology]; Figure 2.25; p. 85; 2017; Günter Dietrich.

Chem. Lett. 1980, 1197-1200.

Appl. Catal. Mar. 1982, 381-388.

Appl. Catal. 1987, 31, 309-321.

Procedia Engineering 2013, 51, 467-472.

Pure & Appl. Chem., 1994, 66, 1739-1758.

F. M. Nelsen and F. T. Eggertsen, Analyt. Chem. 1958, 30, 1387-1390.

S. W. Sing, Adsorption, Surface Area and Porosity, London 1982, chs. 2 and 6.

* cited by examiner

METHOD FOR THE HYDROGENATION OF AROMATIC NITRO COMPOUNDS

CROSS-REFERENCE TO RELATED APPLICATION

This application is a national stage application under 35 U.S.C. § 371 of PCT/EP2020/073991, filed Aug. 27, 2020, which claims the benefit of European Application No. 19194563.3, filed Aug. 30, 2019 and European Application No. 20179290.0, filed Jun. 10, 2020, each of which is incorporated herein by reference.

FIELD

The present invention relates to a process for preparing an aromatic amine by hydrogenating an aromatic nitro compound, comprising the steps of (I) providing a tetraamine-copper-based impregnated catalyst, especially an impregnated catalyst obtainable by the incipient wetness method, comprising a metal or metal oxide on a support as hydrogenation catalyst, where at least metallic or oxidic copper (especially CuO) is present and the molar proportion of Cu based on all metals present is in the range from 0.75 to 1, and where the carrier comprises shaped silicon dioxide bodies or shaped silicon carbide bodies; (II) optionally activating the hydrogenation catalyst by treating with hydrogen in the absence of the aromatic nitro compound; (III) reacting the aromatic nitro compound with hydrogen in the presence of the optionally activated hydrogenation catalyst to obtain the aromatic amine. BACKGROUND The hydrogenation of nitroaromatics to the corresponding aromatic amines with hydrogen has long been known and is of major industrial significance. A representative example is the hydrogenation of nitrobenzene to aniline The majority of the aniline produced globally is used for the production of the di- and polyamines of the diphenylmethane series (MDA), which in turn are intermediates for the production of the important di- and polyisocyanates of the diphenylmethane series (MDI).

The hydrogenation can be conducted in the liquid phase or gas phase, under isothermal or adiabatic conditions. Also known is a combination of isothermal and adiabatic reaction regimes. A series of catalysts has been described in the literature for this purpose. Particular mention should be made here of palladium- and copper-based catalyst systems.

For example, the use of palladium-based catalysts on ceramic supports is known. German patent application DE 28 49 002 A1 describes a process for reduction of nitro compounds in the presence of palladium-containing three-component supported catalysts in cooled tubular reactors. In preferred embodiments, the catalyst contains 1 to 20 g of palladium, 1 to 20 g of vanadium and 1 to 20 g of lead per liter of $\alpha$-$Al_2O_3$. Similar catalysts, but additionally doped with Mo, Re or W, have also been described in DE 197 15 746 A1. EP 1 882 681 A1 discloses that it is advantageous to dope such three-component supported catalysts additionally with a sulfur- or phosphorus-containing, preferably phosphorus-containing, compound (for example the oxygen acids of phosphorus or the alkali metal salts thereof such as, in particular, sodium dihydrogenphosphate, sodium or potassium phosphate, or sodium hypophosphite). International publication WO 2013/030221 A1 describes the advantageous effects of potassium doping of the catalyst on the phenol content of the aniline formed.

The use of copper-based catalysts for the hydrogenation of nitrobenzene in particular has long been known (see U.S.

Pat. Nos. 1,207,802 and 3,136,818). The support used for the catalytically active material was the natural stone pumice, which contains silicates and sodium as its main components.

The use of copper catalysts on silicon dioxide support for the hydrogenation of nitrobenzene to aniline has likewise long been known (e.g. GB 823,026 or U.S. Pat. No. 2,891,094 from the 1950s). Both patents describe the use of copper-ammine complexes as catalyst precursor compounds. For preparation of the catalysts, a hydrogel is precipitated by acidifying a sodium silicate solution, and it is admixed with the copper-ammine complex after filtration and washing. The hydrogel thus treated is filtered off, washed, dried, and calcined in reducing atmosphere. Although the treatment of the hydrogel with the copper-ammine complex is described as impregnation, the procedure described, on account of the finely divided nature of the carrier (in the form of a freshly precipitated hydrogel and therefore not having any pores at all that could take up copper particles), is more of a simple deposition of copper particles on the hydrogel.

A tried-and-tested and frequently employed method of preparing hydrogenation catalysts is impregnation with metal salt solutions, in which the support used has pores that absorb the metal salt solutions. For this purpose, the support is either moistened with the metal salt solution up to a maximum of saturation of its water absorption capacity (called the "incipient wetness" method) or treated in supernatant solution. Impregnation methods are described, for example, in the patent applications that are discussed hereinafter: WO 2010/130604 A2, EP 0 696 573 A1, DE 2 311 114, WO 95/32171 A1 and WO 2009/027135 A1.

International patent application WO 2010/130604 A2 describes a process for preparing aromatic amines, especially aniline, using copper-containing catalysts on $SiO_2$ supports. The process is more particularly characterized in that the $SiO_2$ has been produced by wet grinding, followed by spray drying. The wet grinding process affords silicon dioxide particles having a diameter in the order of magnitude of micrometers, especially in the range from 1 to 35 µm. Such small catalyst diameters are also required for the method described, since the catalysts thus produced are to be used in the form of fluidized bed catalysts, which would not even be practicable with macroscopically appreciable shaped bodies having sizes in the millimeter range. For application of the catalytically active metals, impregnation from supernatant solution is described, for example using ammoniacal carbonate solutions.

EP 0 696 573 A1 describes a process in which aromatic amines are prepared by hydrogenating the corresponding nitroaromatics in the gas phase over fixed bed catalysts. The catalysts contain hydrogenation-active metals on supports that can be prepared by impregnation. The hydrogenation catalyst used is especially a catalyst containing palladium on $\alpha$-$Al_2O_3$, containing 1 to 100 g of Pd per liter of $\alpha$-$Al_2O_3$, preferably precipitated in the form of a shell, where the catalyst may additionally contain vanadium and lead. There is no description of catalysts based on ammine complexes.

German published specification DE 2 311 114 is concerned with the improvement of copper chromite catalysts used for hydrogenation of ketones, carboxylic esters and nitro compounds. What is proposed for this purpose is a process for preparing a copper chromite catalyst applied to supports, which is more particularly characterized in that basic ammonium-copper(II) chromate is formed in the pores of an inorganic oxidic support material by reaction of precursors of basic ammonium-copper(II) chromate that react here with one another, and the support material is then heated to a temperature of about 250 to 500° C. for about 0.1 to 20 hours for conversion of the basic ammonium-copper (II) chromate to copper chromite. According to this document, copper chromite is often represented as "xCuO, $Cr_2O_3$". It is immediately apparent to the person skilled in the art that this is merely a description of the stoichiometric ratios and does not give any information as to the actual structure of the catalyst. There is no disclosure of catalysts having a molar proportion of Cu of 75 mol % or more.

International patent application WO 95/32171 A1 is concerned with the preparation of alcohols by the catalytic hydrogenation of the corresponding carbonyl compounds at elevated temperature and elevated pressure in the liquid phase. Copper catalysts are described for this purpose, these being obtainable by impregnating $SiO_2$-containing support materials with various copper salts that are thermally "readily" decomposable (i.e. below 350° C.), such as copper nitrate, copper carbonate, copper formate, copper oxalate and the readily water-soluble am(m)inic complexes thereof.

International patent application WO 2009/027135 A1 is likewise concerned with the preparation of alcohols by hydrogenation of carbonyl compounds. The hydrogenation catalyst used consists of a support material and at least one hydrogenation-active metal, wherein the support material is based on titanium dioxide, zirconium dioxide, aluminum oxide, silicon oxide or mixed oxides thereof, and the hydrogenation-active metal contains at least one element from the group of copper, cobalt, nickel, chromium, and wherein the support material further comprises the element barium. One example described is the preparation of a copper-containing impregnated catalyst on aluminum oxide with an about 14% tetraamminecopper carbonate solution.

Entirely different from impregnated catalysts are catalyst alloys, for example the known Raney catalysts. WO 98/53910 A1 discloses a shaped activated fixed bed metal catalyst having a pore volume of 0.05 to 1 ml/g and an outer activated shell, consisting of a sintered, finely divided catalyst alloy and optionally promoters, wherein the catalyst alloy includes metallurgical phase domains that result from the preparation of the alloy, the greatest phase of which in terms of volume has a specific interfacial density of more than 0.5 $\mu m^{-1}$.

German patent application DE 39 33 661 A1 is concerned with a catalyst for hydrogenation of acetophenone to methyl benzyl alcohol. The catalyst is prepared by impregnation, which is especially understood to mean spraying, of a silicon dioxide support with a solution of tetraaminecopper carbonate and a solution of ammonium chromate or mixtures thereof, followed by drying.

German patent application DE 10 2010 029 924 A1 is concerned with the regeneration of copper-, chromium- and/or nickel-containing hydrogenation catalysts as used in the preparation of higher alcohols, especially those having 8 to 13 carbon atoms, by catalytic hydroformylation (also referred to as the oxo process) of the olefins having one carbon atom fewer, followed by hydrogenation of the aldehydes formed.

British patent GB 825,602 is concerned with the dehydrogenation of alcohols to aldehydes and ketones, using a catalyst containing reduced copper oxide and small amounts of non-reduced copper oxide, and also "alkali metal oxides". The catalyst is prepared by heating a tetraamminecopper complex, followed by heating under hydrogen.

European patent application EP 3 320 969 A1 is concerned with chromium- and nickel-free catalysts for heterogeneous hydrogenation of oxo process aldehydes. The catalysts contain only copper, but it is necessary for the support material used to be silicon dioxide and for the content of Cu and $SiO_2$ in the active catalyst to be set accurately within very narrow limits.

In addition to use as catalysts for a wide variety of different reactions, copper compounds are also employed in many other fields, for example as a fungicide (see, for instance, U.S. Pat. No. 3,900,504).

The study of copper catalysts for various applications is also addressed by various articles from the non-patent literature. Examples include *Chem. Lett.* 1980, 1197-1200, *Appl. Catal.* 1982, 3, 381-388, *Appl. Catal.* 1987, 31, 309-321 and *Procedia Engineering* 2013, 51, 467-472.

In addition to the use of palladium- or copper-based catalysts, the use of catalysts containing both metals is also known. One example of this is described in British patent GB 961,394. This describes catalysts for the treatment of motor vehicle exhaust gas, containing 0.5% to 25% copper and 0.01% to 3% palladium.

The prior art catalysts described for the hydrogenation of nitroaromatics, especially of nitrobenzene, are suitable in principle for this purpose, but there is still potential for improvement with regard to selectivity and long-term stability. The emphasis here was on the copper-based catalysts that are less expensive compared to the known palladium-based catalysts.

SUMMARY

Taking account of the above, the present invention has for its subject matter a process for preparing an aromatic amine, especially aniline, by hydrogenating an aromatic nitro compound, especially nitrobenzene, comprising the following steps:

(I) providing a tetraamminecopper salt-based impregnated catalyst, especially an impregnated catalyst obtainable (preferably prepared) by the incipient wetness method, comprising a metal or metal oxide on a support as hydrogenation catalyst, where at least metallic or oxidic copper (especially CuO) is present and the molar proportion of Cu based on all metals present is in the range from 0.75 to 1, preferably 0.90 to 1, and where the carrier comprises shaped silicon dioxide bodies or shaped silicon carbide bodies;

(II) optionally (and preferably) activating the hydrogenation catalyst by treating with hydrogen in the absence of the aromatic nitro compound;

(III) reacting the aromatic nitro compound with hydrogen in the presence of the optionally activated hydrogenation catalyst to obtain the aromatic amine.

In the terminology of the present invention, a tetraamminecopper salt-based impregnated catalyst comprising a metal or metal oxide on a support is understood to mean a catalyst that has been obtained by impregnating a support with an aqueous, especially ammoniacal, solution of a tetraamminecopper salt (i.e. a salt containing the tetraammine complex of $Cu^{II}$, $[Cu^{II}(NH_3)_4]^{2+}$, as cation), followed by drying and calcining (preferably in oxygen-containing atmosphere). The support is impregnated by mixing it with the aqueous, especially ammoniacal, solution of a tetraamminecopper salt (by introducing the support into the tetraamminecopper salt solution, or pouring the solution over the support). The nature of the support and the amount of the aqueous, especially ammoniacal, solution of the tetraamminecopper salt are matched here to one another in such a way that either (=impregnation in supernatant solution) there is more tetraamminecopper salt solution present than the pores of the support (see also the section further down relating to shaped bodies) can accommodate, or (=incipient wetness method— preferred method) there is a maximum of just as much (preferably somewhat less, especially 2% to 5% less) tetraamminecopper salt solution as the pores of the support can accommodate.

In referring to such an impregnation of the support, it should be noted that, in the terminology of the present invention, the term impregnation is limited to that as described above and does not serve, for instance, as is variously the case in the specialist literature, as a collective term for virtually any kind of application of hydrogenation-active substances on a support.

The impregnated catalyst is therefore especially one obtainable by the incipient wetness method mentioned (and preferably one that has indeed been produced by this method). In other words, this means that, in the process for production of the impregnated catalyst, the support is preferably impregnated with the aqueous, especially ammoniacal, solution of a tetraamminecopper salt in such a way as not to exceed the maximum absorptivity of the support determined by means of saturation with water, and preferably as to undershoot it by not more than 5% and further preferably by at least 2%. Means of determining the maximum absorptivity of the support determined by means of saturation with water are known in the specialist field. What is crucial for the purposes of the present invention is the method described at the start of the examples in the section "Determining the maximum absorptivity of the support".

According to the invention, the support comprises shaped silicon dioxide or silicon carbide bodies, a shaped body in this context being understood to mean that the support is in the form of discrete (i.e. macroscopically appreciable) particles having average diameters especially in the range from 1.0 mm to 15 mm, preferably in the range from 4.0 mm to 10 mm. Examples especially include shaped cylindrical bodies and shaped spherical bodies, where the diameter of the base in the case of shaped cylindrical bodies is regarded as the diameter in this context and the length of the shaped cylindrical bodies is always greater than the diameter. In the case of shaped cylindrical bodies, the individual cylinders may also be combined to form aggregates comprising multiple cylinders, especially to give trilobes (aggregates composed of three cylinders joined to one another in longitudinal direction). In the case of such aggregates of cylinders, the diameter is considered to be the diameter of a theoretical circle encircling the bases of the mutually joined cylinders.

Such shaped bodies are different than both unshaped structures (such as dust or hydrogels) and monolithic structures. The shaped silicon dioxide or silicon carbide bodies contain pores into which the aqueous solution of the tetraamminecopper salt penetrates. Silicon dioxide ($SiO_2$), as used in the terminology of the present invention, is typically referred to in the English-language literature as silica.

The molar proportion of Cu based on all metals present (=x(Cu)) is based in each case on the metals as such, i.e.

$$x(Cu) = \frac{\text{molar amount } Cu}{\text{Sum of the molar amounts of all metals present}}.$$

The proportions by mass of the metals present on the catalyst are known from the preparation; the molar proportion of copper x(Cu) can easily be calculated therefrom. If no other metal is present other than copper (which is preferred), x(Cu) is 1.

What follows first is a brief summary of different possible embodiments of the invention, although the enumeration of embodiments should be considered to be nonexhaustive:

In a first embodiment of the invention, which may be combined with all other embodiments, step (II) is conducted and the treatment with hydrogen is effected at temperatures in the range from 180° C. to 240° C.

In a second embodiment of the invention, which may be combined with all other embodiments, step (III) is performed adiabatically at temperatures in the range from 160° C. to 500° C., preferably 180° C. to 450° C., more preferably 200° C. to 400° C., or isothermally at temperatures in the range from 180° C. to 550° C., preferably 200° C. to 500° C., more preferably 220° C. to 450° C.

In a third embodiment of the invention, which may be combined with all other embodiments, especially with the second, step (III) is performed adiabatically at a molar ratio of hydrogen to nitro groups in the range from 10 to 200, preferably from 20 to 150, more preferably from 60 to 120, or isothermally at a molar ratio of hydrogen to nitro groups in the range from 3 to 100, preferably from 6 to 60, more preferably from 10 to 30.

In a fourth embodiment of the invention, which may be combined with all other embodiments, the proportion by mass of copper compounds, calculated as metallic Cu, of the hydrogenation catalyst provided in (I), based on the total mass thereof, is in the range from 3% to 35%, preferably 7% to 30%, more preferably 11% to 25%.

In a fifth embodiment of the invention, which may be combined with all other embodiments to the extent that these comprise shaped silicon dioxide bodies as supports, the support comprising shaped silicon dioxide bodies has a specific surface area in the range from 100 $m^2/g$ to 350 $m^2/g$, preferably in the range from 100 $m^2/g$ to 300 $m^2/g$, a pore volume in the range from 0.3 $cm^3/g$ to 1.5 $cm^3/g$, preferably in the range from 0.3 $cm^3/g$ to 1.4 $cm^3/g$, and a side crushing strength in the range from 40 N to 500 N, preferably in the range from 40 N to 350 N.

In a sixth embodiment of the invention, which may be combined with all other embodiments, the hydrogenation catalyst used is a tetraamminecopper carbonate-based impregnated catalyst.

In a seventh embodiment of the invention, which is a particular configuration of the sixth embodiment, the hydrogenation catalyst used is a tetraamminecopper carbonate/ammonium carbonate-based impregnated catalyst or a tetraamminecopper carbonate/ammonium acetate-based impregnated catalyst, preferably a tetraamminecopper carbonate/ammonium carbonate-based impregnated catalyst.

In an eighth embodiment of the invention, which may be combined with all other embodiments, step (I) comprises:

(a) dissolving a copper salt in aqueous ammonia to obtain an alkaline ammoniacal copper salt solution;

(b) impregnating the support with the alkaline ammoniacal copper salt solution obtained in (a), followed by drying of the impregnated support thus obtained to obtain a catalyst precursor, (c) calcining the catalyst precursor obtained in (c) to form the tetraamminecopper-based impregnated catalyst.

In a ninth embodiment of the invention, which is a particular configuration of the eighth embodiment, the copper salt comprises basic copper carbonate.

In a tenth embodiment of the invention, which is a particular configuration of the eighth and ninth embodiments, ammonium carbonate is also dissolved in the aqueous ammonia in addition to the copper salt in step (I)(a).

In an eleventh embodiment of the invention, which is a particular configuration of the eighth to tenth embodiments, the dissolving in step (I)(a) is conducted at temperatures in the range from 0.0° C. to 10.0° C., preferably 1.0° C. to 5.0° C.

In a twelfth embodiment of the invention, which is a particular configuration of the eighth to eleventh embodiments, the drying in step (I)(b) is conducted at temperatures in the range from 80° C. to 150° C., preferably in the range from 90° C. to 130° C., more preferably in the range from 100° C. to 120° C.

In a thirteenth embodiment of the invention, which is a particular configuration of the eighth to twelfth embodiments, the calcining in step (I)(c) is conducted at temperatures in the range from 300° C. to 600° C., preferably in the range from 350° C. to 550° C., more preferably in the range from 400° C. to 500° C.

In a fourteenth embodiment of the invention, which is a particular configuration of the eighth to thirteenth embodiments, the alkaline ammoniacal copper salt solution used for impregnation has a pH (20° C.) in the range from 7.0 to 14, preferably from 8.0 to 12, more preferably from 9.0 to 11.

In a fifteenth embodiment of the invention, which can be combined with all other embodiments, the shaped silicon dioxide bodies or shaped silicon carbide bodies have an average diameter in the range from 1.0 mm to 15 mm, preferably in the range from 4.0 mm to 10.0 mm In a sixteenth embodiment of the invention, which can be combined with all other embodiments, especially with the fifteenth, to the extent that these embodiments comprise shaped silicon dioxide bodies as support, the shaped silicon dioxide bodies are obtainable by:

(i) precipitating silicon dioxide out of a silicate solution and isolating the precipitated silicon dioxide;
(ii) drying the silicon dioxide;
(iii) processing the dried silicon dioxide to give shaped bodies;
(iv) calcining the shaped bodies, preferably at a temperature in the range from 500° C. to 1000° C.

In a seventeenth embodiment of the invention, which may be combined with all other embodiments, an aromatic nitro compound of the formula

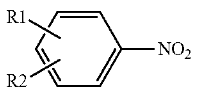

is hydrogenated, in which R1 and R2 are independently hydrogen, methyl or ethyl, where R2 may additionally also be $NO_2$.

In an eighteenth embodiment of the invention, which may be combined with all other embodiments, nitrobenzene is hydrogenated to aniline In a nineteenth embodiment of the invention, which may be combined with all embodiments comprising step (b), the support is impregnated in step (b) with the ammoniacal copper salt solution obtained in (a) in such a way as not to exceed the maximum absorptivity of the support determined by means of saturation with water (=incipient wetness method).

In a twentieth embodiment of the invention, which is a particular configuration of the nineteenth embodiment, the maximum absorptivity of the support is undershot by not more than 5%.

In a twenty-first embodiment of the invention, which is a particular configuration of the eighteenth and nineteenth embodiments, the maximum absorptivity of the support is undershot by at least 2%.

In a twenty-second embodiment of the invention, which can be combined with all other embodiments, the optionally activated hydrogenation catalyst is disposed in a fixed catalyst bed in step (III).

DETAILED DESCRIPTION

The embodiments briefly outlined above and further possible configurations of the invention are elucidated in detail hereinafter. Various embodiments are combinable with one another as desired unless the opposite is clearly apparent to those skilled in the art from the context.

Provision of the Catalyst for Performance of the Hydrogenation

Step (I) of the process of the invention comprises the providing of the tetraamminecopper salt-based impregnation catalyst comprising CuO on shaped silicon dioxide bodies as support. Such catalysts are storage- and transport-stable; therefore, the preparation of the catalyst can be entirely decoupled from the actual hydrogenation and can be effected, for example, at a different site.

Production of the Support

Shaped silicon dioxide bodies suitable as support are producible by methods known to those skilled in the art and are commercially available.

The shaped silicon dioxide bodies are preferably obtained by precipitating finely divided silicon dioxide from aqueous silicate solutions (production of a gel). The precipitated finely divided silicon dioxide is isolated and dried to give silicon dioxide powder. For production of shaped silicon dioxide bodies from the silicon dioxide powder, the latter is processed further to shaped bodies in a manner known to the person skilled in the art, preferably extruded or pelletized. The shaped bodies can be obtained in different three-dimensional forms; for example as cylinders (including aggregates of cylinders such as the abovementioned trilobes) or spheres. Any slight variances that exist from the ideal cylindrical or spherical geometry do not of course leave the scope of the invention.

Shaped silicon carbide bodies suitable as support are producible by methods known to those skilled in the art and are commercially available, where the purity of the materials may vary. Especially suitable is β-silicon carbide in mesoporous form (i.e. having a pore diameter in the range from 2 nm to 50 nm). The definition of "mesoporous" used in the context of the present invention follows the corresponding IUPAC recommendation (see *Pure & Appl. Chem.,* 1994, 66, 1739-1758).

The processing to give shaped silicon dioxide or silicon carbide bodies is preferably followed by a calcination step, preferably at temperatures in the range from 300° C. to 1000° C. The calcination can be conducted in an oxygen-containing atmosphere (especially in air), in a hydrogen atmosphere or in an inert atmosphere (especially in nitrogen or noble gas atmosphere). Calcination in an oxygen-containing atmosphere is preferred.

Preferably, shaped bodies in the form of cylinders (after calcination, if conducted) have an average length in the range from 3.0 mm to 18 mm, preferably in the range from 6.0 mm to 14 mm, and an average diameter in the range from 1.0 mm to 15 mm, preferably in the range from 4.0 mm to 10 mm. This can be achieved by establishing appropriate conditions in the extrusion and verified by simple measurement (for example by means of a caliper gauge).

Preferably, shaped bodies in spherical form (after calcination, if conducted) have an average particle size (i.e. the average size of the shaped bodies =average diameter) $x_{50,3}$ in the range from 1.0 mm to 15 mm, more preferably in the range from 4.0 mm to 10.0 mm. This can be achieved by establishing appropriate conditions in the pelletization and/or by sieving. Whether the desired average particle size is indeed present can be verified by a particle size analysis. The crucial test method in this regard in the context of the invention is sieve analysis. The average particle size used here is the mass-based value ("$x_{50,3}$"). The procedure for determination of the average particle size is that a representative sample of the particles (=shaped bodies) is first subjected to a sieve analysis, and the result is evaluated on the basis of mass. The sieve analysis is effected using a vibratory sieving machine (e.g. AS 200 digit model from Retsch) in which the analysis sieves are arranged one on top of another with increasing mesh size to form a set of sieves. The selection of the analysis sieves (diameter and mesh size) depends primarily on the amount of material to be sieved and the expected particle size distribution (preliminary tests may be necessary). The number of sieves and the graduations of the nominal opening widths should be selected such that the entire particle spectrum of the sample if at all possible is divided into fractions. In the performance of the sieve analysis, it should be ensured that the maximum passage of material to be sieved (optimal quality of sieving-out) is achieved. If required (for example if new particles with which there is no operating experience as yet are to be used), it is necessary to experimentally ascertain suitable sieving times and amplitudes in preliminary tests. A first indication of the amplitude is found from the observation of the movement of material being sieved. The movement should be neither too weak nor too strong. The optimal sieving time has been attained when the mass of the material passing through the sieve, within one minute, changes by less than 0.1% of the amount applied (DIN 66165, version of April 1987). The person skilled in the art is familiar with the methods outlined merely briefly here. The result of the sieve analysis is the particle size distribution of the particles analyzed. The result is preferably presented as a graph by plotting the proportion by mass of the individual fractions ("$p_3$") in a bar chart and the cumulative curve of the percentages ("$Q_3$") against the nominal sieve opening widths (x). The person skilled in the art is easily able to calculate the median particle size $x_{50,3}$ (i.e. 50% by mass of the particles are smaller than the corresponding value x), either manually or preferably by means of computer-assisted evaluation programs.

A support comprising shaped silicon dioxide bodies (after calcination if conducted) preferably has a specific surface area in the range from 100 $m^2/g$ to 350 $m^2/g$, more preferably in the range from 100 $m^2/g$ to 300 $m^2/g$ (determined according to F. M. Nelsen and F. T. Eggertsen, Analyt. Chem. 1958, 30, 1387 — 1392), a pore volume in the range from 0.3 $cm^3/g$ to 1.4 $cm^3/g$, preferably in the range from 0.3 $cm^3/g$ to 1.4 $cm^3/g$ (determined according to and S. W. Sing, Adsorption, Surface Area and Porosity, London 1982, chs. 2 and 6) and a side crushing strength in the range from 40 N to 500 N, preferably in the range from 40 N to 350 N (determined to DIN 50 106 in the version of November 2016; this method described for metallic materials is also suitable for the supports of relevance to the invention). For supports comprising mesoporous shaped β-silicon carbide bodies that are usable in accordance with the invention, comparable values are applicable except for the BET surface area. The BET surface area here is typically lower and is preferably in the range from 20 $m^2/g$ to 30 $m^2/g$.

Preparation of the Solution of the Tetraamminecopper Salt

Methods of preparing tetraamminecopper salts are known in principle in the prior art. Outlined hereinafter is a preferred procedure.

The starting copper salt used is preferably basic copper carbonate. However, other copper salts such as copper hydroxide and copper acetate are also usable. It is also possible to use mixtures of copper salts. The copper salt is dissolved in an aqueous ammonia to obtain an ammoniacal copper salt solution. The aqueous ammonia preferably has a proportion by mass of ammonia in the range from 15% to 30%, more preferably in the range from 20% to 30%, most preferably in the range from 25% to 30%.

It is advisable to stabilize the tetraamminecopper complex by maintaining a pH (20° C.) in the range from 7.0 to 14, preferably in the range from 8.0 to 12, more preferably in the range from 9.0 to 11. It is therefore preferable to add a portion of the ammonia required for complexation in the form of ammonium carbonate or ammonium acetate, preferably ammonium carbonate, and hence to limit the increase in the pH (buffering). Preference is given to adding a sufficient amount of ammonium carbonate or ammonium acetate that the desired pH is attained after addition of the copper salt and complexation. By addition of aqueous ammonia, it is possible to increase the pH subsequently after the mixing. The solution of the tetraamminecopper salt is to be prepared at low temperatures in order to prevent outgassing of ammonia. Temperatures in the range from 0.0° C. to 10.0° C., preferably in the range from 1.0° C. to 5.0° C., have been found to be useful.

The procedure is more preferably as follows:

The copper salt, ammonium carbonate and 80% of the calculated ammonia solution are first mixed at 5.0° C. While stirring, further ammonia solution (cooled to 5.0° C.) is added until a pH of 9.2 (see also Hartinger, *Handbuch Abwasser and Recyclingtechnik* [*Handbook of Wastewater and Recycling Technology*]; FIG. 2.25; p. 85; 2017; Gunter Dietrich) has been attained.

Preparation of the Catalyst From the Support and Solution of the Tetraamminecopper Salt The impregnation of the support required as the first step can in principle be effected by known methods. It is possible either to employ the above-described incipient wetness method and impregnation in supernatant solution. Preference is given to using the incipient wetness method, especially in a variant in which the support, in an impregnation step (i.e. in the case of multiple impregnation steps: in each of the impregnation steps), is treated only with such an amount of the impregnation solution that is slightly (e.g. 2% to 5%) below the above-determined maximum absorptivity of the support (see the examples section for the determination of maximum absorptivity). Impregnation in multiple steps is also possible if the aim is to achieve particularly high copper contents. However, preference is given to conducting not more than two impregnation steps. The impregnation is followed by drying (especially at temperatures in the range from 80° C. to 150° C., preferably in the range from 90° C. to 130° C., more preferably in the range from 100° C. to 120° C.). This affords a precursor of the hydrogenation catalyst.

This precursor is used to obtain, by calcining, the tetraamminecopper-based impregnated catalyst on a support comprising shaped silicon dioxide bodies or shaped silicon carbide bodies. The calcination is especially effected at temperatures in the range from 300° C. to 600° C., preferably in the range from 350° C. to 550° C., more preferably in the range from 400° C. to 500° C. The calcination can be conducted in an oxygen-containing atmosphere (especially in air), in a hydrogen atmosphere or in an inert atmosphere (especially in nitrogen or noble gas atmosphere). Calcination in an oxygen-containing atmosphere is preferred. The calcination conditions determine the form in which the copper is present on the catalyst; in the case of calcination under oxidizing conditions the copper is predominantly to entirely oxidic, especially CuO, and in the case of calcination under reducing conditions the copper is predominantly to entirely metallic.

The number of impregnation steps and the concentration of the solution of the tetraamminecopper salt are preferably matched to one another in such a way that the hydrogenation catalyst, based on the total mass thereof, after calcination, has a proportion by mass of copper compounds (present in total in the hydrogenation catalyst), calculated as metallic Cu, in the range from 3% to 35%, preferably 7% to 30%, more preferably 11% to 25%.

Hydrogenation Procedure

Nitroaromatics

The process of the invention is suitable in principle for hydrogenation of all nitroaromatics of industrial relevance to the corresponding aromatic amines More preferably, nitroaromatics of the following formula are hydrogenated:

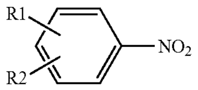

where R1 and R2 are independently hydrogen, methyl or ethyl, where R2 may additionally also be $NO_2$. Particular preference is given to the hydrogenation of nitrobenzene (R1=R2=H) to aniline

Activation of the Catalyst (Optionally as a Separate Step)

Prior to commencement of the actual hydrogenation, it is preferable to reduce the hydrogenation catalyst with hydrogen, especially at temperatures in the range from 180° C. to 240° C., and hence convert it to its "active form" (to activate it; step (II) of the process of the invention). Since the catalyst is subjected to reducing conditions in the actual hydrogenation as well, there is no absolute need for activation as a separate step upstream of the actual hydrogenation. However, the performance of the upstream step (II) leads to improved instantaneous selectivities on commencement of the hydrogenation. The activation preferably follows inertization of the reactor by an inert gas (especially nitrogen) with a hydrogen stream of pressure in the range from 1.0 $bar_{(abs.)}$ to 3.0 $bar_{(abs.)}$, for example 1.5 $bar_{(abs.)}$, where the increase in temperature on the catalyst by activation should not exceed 30° C. through stepwise addition of the hydrogen. The activation is effected until the exothermic reaction is not observed any longer after addition of 100% hydrogen. This step is preferably effected directly in the reactor envisaged for the actual hydrogenation (see below).

Hydrogenation

Step (III) of the process of the invention, the reaction of the aromatic nitro compound with hydrogen (=hydrogenation) in the presence of the preferably activated hydrogenation catalyst to obtain the aromatic amine, can in principle be effected as known from the prior art.

The hydrogenation is effected in an apparatus envisaged for the purpose, the hydrogenation reactor or reactor for short. Suitable reactors are sufficiently well known to those skilled in the art.

The hydrogenation of the aromatic nitro compound is preferably effected continuously. If the hydrogen is used in a superstoichiometric amount, preference is given to recycling unconverted hydrogen into the reaction. The reaction can be effected in the liquid phase and in the gas phase. Performance of the reaction in the gas phase is preferred.

The hydrogenation can be conducted adiabatically or isothermally. In the case of an adiabatic mode of operation, there is no specific supply of heat or removal of heat. Therefore, the enthalpy of reaction—apart from unavoidable heat losses, which are preferably minimized by insulation of the reactor—is reflected quantitatively in the temperature differential between the reaction mixture and the product mixture (adiabatic temperature jump). By contrast, in the isothermal mode of operation, the temperature—apart from unavoidable local "hotspots"—is kept constant by external indirect cooling. Possible reaction regimes that can also be employed in the process of the invention are described in EP 0 944 578 A2 (isothermal mode of operation) and in EP 0 696 574 A1, EP 0 696 573 A1, and in EP 1 882 681 A1 (adiabatic mode of operation). Particular preference is given to observing the following conditions that have been found to be useful especially for a reaction in the gas phase: Step (III) is conducted adiabatically at temperatures in the range from 160° C. to 500° C., preferably 180° C. to 450° C., more preferably 200° C. to 400° C., or isothermally at temperatures in the range from 180° C. to 550° C., preferably 200° C. to 500° C., more preferably 220° C. to 450° C.

With regard to the molar ratio of hydrogen to nitro groups, it will be apparent that this must be at least stoichiometric, i.e. at least 3 (=3:1), for achievement of complete conversion of nitroaromatics. However, it has been found to be useful to use hydrogen in a superstoichiometric amount, generally choosing a particularly high excess beyond stoichiometry in adiabatic mode, in order to allow the considerable heat of reaction to be absorbed by this excess hydrogen. More particularly, the present invention therefore also relates to a process in which step (III) is conducted adiabatically at a molar ratio of hydrogen to nitro groups in the range from 10 to 200, preferably from 20 to 150, more preferably from 60 to 120, or isothermally at a molar ratio of hydrogen to nitro groups in the range from 3 to 100, preferably from 6 to 60, more preferably from 10 to 30.

Preferred reactors for an isothermally operated reactor are thermostatted tubular reactors or shell and tube reactors. Suitable embodiments of such reactors are described, for example, in DE 2 201 528 A1, DE 2 207 166 A1, DE 198 06 810 A1, EP 1 439 901 A1, EP 1 569 745 A1, EP 1 590 076 A1, EP 1 587 612 A1, EP 1 586 370 A1, EP 1 627 678 A1 or DE 202 006 014 116 U1.

Preferred reactors for an adiabatically operated reactor are those described in DE 10 2006 035 203, paragraphs [0030] to [0033].

Irrespective of the mode of operation (isothermal or adiabatic), it is preferable to arrange the hydrogenation catalyst in step (III) in a fixed catalyst bed. This means that the shaped bodies are at a fixed position in the reactor used, for example are arranged within thermostatted reaction tubes (isothermally operated tubular reactors and shell and tube reactors) or on a support grid, especially between two support grids (adiabatically operated reactors containing catalyst beds). The counterpart to such fixed bed reactors are fluidized bed reactors (as used, for example, in WO 2010/130604 A2), in which very finely divided catalyst particles (with average sizes in the micrometer range) are set in swirling motion.

The invention is elucidated in detail hereinafter with the aid of examples.

EXAMPLES

General Methods

Determination of Maximum Absorptivity of the Support

The absorptivity maximum is determined by weighing the shaped bodies before and after absorption of water, as described hereinafter. For this purpose, the support material is weighed out and, in a vessel that enables visual observation (e.g. glass beaker), left to stand (without moving the vessel) blanketed with demineralized water until no further air bubbles ascend. The supernatant water is decanted, and the surface of the still-moist shaped bodies is dried. This is done by absorbing the moisture adhering to the surface with filter paper, which, according to the shape of the shaped bodies, can be performed by rolling on or dabbing with the filter paper. This drying step removes water adhering to the surface, but not water that has been absorbed into the pores of the support. By weighing the contents and subtracting the starting weight, the water absorption in grams is obtained, corresponding to the absorptivity maximum of the shaped body used.

In all examples for catalyst preparation, the amount of the metal salt solution to be used for impregnation was adjusted such that it was 2% below the maximum absorptivity (incipient wetness method).

Starting Materials $Cu(NO_3)_2$ solution from Poletto Aldo with a density at 20° C. of 1.48 g/ml, a Cu content of (14.5±0.5)% by mass and a pH (measured at ambient temperature, 20 to 25° C.) of 3.5±0.5.

Shaped silicon dioxide bodies, 3×5 mm cylinders, absorptivity 1.13 ml/g, bulk density 417 g/l.

Example 1

Preparation of a Copper Nitrate-Based Impregnated Catalyst as Comparative Catalyst 100 ml of the silicon dioxide support was impregnated with the $Cu(NO_3)_2$ solution. This involved agitating the mixture until the liquid had been completely absorbed by the support material. The impregnated shaped bodies were dried to constant mass at 120° C. and then calcined at 450° C. in air atmosphere for 4 h. The catalyst had a proportion by mass of copper compounds, calculated as metallic copper, of about 24.0%.

Example 2

Hydrogenation of Nitrobenzene With the Catalyst From Example 1 (Comparison)

The catalyst from example 1 was transferred into a fixed bed reactor in the oxidized state, and nitrogen was passed through it until the remaining oxygen had been driven out. The temperature was adjusted to a value in the range from 200° C. to 240° C., and the activation was commenced by metering in hydrogen. The exothermicity caused by the reaction should be kept as low as possible. On conclusion of the activation, nitrogen was passed through the catalyst to remove the excess hydrogen. For the reaction, nitrobenzene (NB) was metered into the activated catalyst, successively increasing and adjusting the amount of nitrobenzene to the target load of 0.9 $g_{NB}$ $ml_{cat}^{-1}$ $h^{-1}$. The molar hydrogen:nitrobenzene ratio was 10:1. The reaction was conducted polytropically, with removal of the heat formed in the reaction by a heat carrier. The hydrogenation was conducted in each case until breakthrough of nitrobenzene was observed.

The catalyst described in example 1 showed a service life of 60 h and an average aniline selectivity of 99.2%.

Example 3

Preparation of a Tetraamminecopper-Based Impregnated Catalyst as Hydrogenation Catalyst for the Process of the Invention Compositions used for a solution with a proportion by mass of Cu of (12.7±0.5)% at pH=9.2±1.0:

ammonium carbonate 65.785 g
basic copper carbonate 74.6 g
ammonia 81.7 g
demineralized water 100 g First of all, the starting materials were cooled to below 5° C. in a refrigerator. Water and ammonia were mixed in a closable vessel. The solids were weighed out together in a dish and added rapidly to the cooled ammonia solution, and they were mixed together with the lid closed until the salts had dissolved.

100 ml of the silicon dioxide support was impregnated with an amount of the tetraamminecopper carbonate solution thus prepared corresponding to the absorptivity of the support. This involved agitating the mixture until the liquid had been completely absorbed by the support material. The impregnated shaped bodies were dried to constant mass at 120° C. and then calcined at 450° C. for 4 h.

The catalyst had a proportion by mass of copper compounds, calculated as metallic copper, of about 14.8%.

Example 4

Hydrogenation of Nitrobenzene With the Catalyst From Example 3 (Inventive)

Apart from the catalyst, the experiment was conducted analogously to example 2; the service life was 295 h and the average aniline selectivity 99.6%.

Example 5

Preparation of a Tetraamminecopper-Based Impregnated Catalyst as Hydrogenation Catalyst for the Process of the Invention at pH 10

Proceeding from example 3, a catalyst was prepared that was prepared at pH=10. The following amounts were used:

ammonium carbonate: 15.8 g
basic copper carbonate: 18.18 g
ammonia: 32.60 g
demineralized water: 33.42 g First of all, the starting materials were cooled to below 5° C. in a refrigerator. Water and ammonia were mixed in a closable vessel. The solids were weighed out together in a dish and added rapidly to the cooled ammonia solution, and they were mixed together with the lid closed until the salts had dissolved.

100 ml of the silicon dioxide support was impregnated with an amount of the tetraamminecopper carbonate solution thus prepared corresponding to the absorptivity of the support. This involved agitating the mixture until the liquid had been completely absorbed by the support material. The impregnated shaped bodies were dried to constant mass at 120° C. and then calcined at 450° C. for 4 h. The catalyst had a proportion by mass of Cu of about 12.4%.

Example 6

Hydrogenation of Nitrobenzene With the Catalyst From Example 5 (Inventive)

Apart from the catalyst, the experiment was conducted analogously to example 2; the service life was 240 h and the average aniline selectivity 99.6%.

Example 7

Preparation of a Tetraamminecopper-Based Impregnated Catalyst as Hydrogenation Catalyst for the Process of the Invention at pH 10 Including "Aging"

A catalyst was prepared analogously to example 5, except that the catalyst, in the impregnation process, was left to stand in the wet state for one week prior to drying.

Example 8

Hydrogenation of Nitrobenzene With the Catalyst From Example 7 (Inventive)

Apart from the catalyst, the experiment was conducted analogously to example 2; the service life was 240 h and the average aniline selectivity had a value of 99.5%.

Example 9

Preparation of a Tetraamminecopper-Based Impregnated Catalyst as Hydrogenation Catalyst for the Process of the Invention at pH 10 With Multiple Impregnation The procedure was analogous to example 5, except that a higher copper content was achieved by double impregnation. The proportion by mass of copper compounds, calculated as metallic copper, after calcination was about 22%.

Example 10

Hydrogenation of Nitrobenzene With the Catalyst From Example 9 (Inventive)

Apart from the catalyst, the experiment was conducted analogously to example 2; the service life was 360 h and the average aniline selectivity 99.6%.

Example 11

Preparation of a Tetraamminecopper-Based Impregnated Catalyst as Hydrogenation Catalyst for the Process of the Invention at pH 9.2 With Multiple Impregnation at Lower Metal Concentration The procedure was analogous to example 5, except that a double impregnation was conducted at a lower metal content of the impregnation solution. The proportion by mass of copper compounds, calculated as metallic copper, after calcination was about 15.3%.

Example 12

Hydrogenation of Nitrobenzene With the Catalyst From Example 11 (Inventive)

Apart from the catalyst, the experiment was conducted analogously to example 2; the service life was 290 h and the average aniline selectivity had a value of 99.6%.

Example 13

Preparation of a Tetraamminecopper-Based Impregnated Catalyst as Hydrogenation Catalyst for the Process of the Invention at pH 9.2 on an Alternative Silica Support The procedure was analogous to example 3, except that an alternative silica support material having a lower specific surface area of 80 $m^2/g$ was used. The proportion by mass of copper compounds, calculated as metallic copper, after calcination was about 12.9%.

Example 14

Hydrogenation of Nitrobenzene With the Catalyst From Example 13 (Inventive)

Apart from the catalyst, the experiment was conducted analogously to example 2; the service life was 260 h and the average aniline selectivity had a value of 99.5%.

Example 15

Preparation of a Tetraamminecopper-Based Impregnated Catalyst as Hydrogenation Catalyst for the Process of the Invention at pH 10 on a "Trilobe" Shaped Body The procedure was analogous to example 5, except that the support material used was a silica-based trilobe shaped body. The proportion by mass of copper compounds, calculated as metallic copper, after calcination was about 11.6%.

Example 16

Hydrogenation of Nitrobenzene With the Catalyst From Example 15 (Inventive)

Apart from the catalyst, the experiment was conducted analogously to example 2; the service life was 240 h and the average aniline selectivity 99.7%.

Example 17

Preparation of a Tetraamminecopper-Based Impregnated Catalyst as Hydrogenation Catalyst for the Process of the Invention at pH 10 With Multiple Impregnation on a "Trilobe" Shaped Body The procedure was analogous to example 5, except that the support material used was a silica-based trilobe shaped body and a multiple impregnation was conducted. The proportion by mass of copper compounds, calculated as metallic copper, after calcination was about 19.6%.

Example 18

Hydrogenation of Nitrobenzene With the Catalyst From Example 17 (Inventive)

Apart from the catalyst, the experiment was conducted analogously to example 2; the service life was 300 h and the average aniline selectivity had a value of 99.7%.

Example 19

Preparation of a Tetraamminecopper-Based Impregnated Catalyst as Hydrogenation Catalyst for the Process of the Invention at pH 10 With Multiple Impregnation on a Silicon Carbide Support of Comparatively Low Purity (about 99.5% SiC)

The procedure was analogous to example 5, except that the support material used was a silicon carbide support (about 99.5% SiC) and a multiple impregnation was conducted. The proportion by mass of copper compounds, calculated as metallic copper, after calcination was about 10.3%.

Example 20

Hydrogenation of Nitrobenzene With the Catalyst From Example 19 (Inventive)

Apart from the catalyst, the experiment was conducted analogously to example 2; the service life was 290 h and the average aniline selectivity had a value of 99.8%.

Example 21

Preparation of a Tetraamminecopper-Based Impregnated Catalyst as Hydrogenation Catalyst for the Process of the Invention at pH 10 With Multiple Impregnation on a Silicon Carbide Support of Hither Purity Compared to Example 19 (≥99.85% SiC)

The procedure was analogous to example 5, except that the support material used was a silicon carbide support (≥99.85% SiC) and a multiple impregnation was conducted. The proportion by mass of copper compounds, calculated as metallic copper, after calcination was about 10.1%.

Example 22

Hydrogenation of Nitrobenzene With the Catalyst From Example 21 (Inventive)

Apart from the catalyst, the experiment was conducted analogously to example 2; the service life was 240 h and the average aniline selectivity had a value of 99.8%.

The invention claimed is:

1. A process for preparing an aromatic amine by hydrogenating an aromatic nitro compound, comprising:

(I) providing a tetraamminecopper salt-based impregnated catalyst comprising a metal or metal oxide on a support as hydrogenation catalyst, where at least metallic or oxidic copper is present and the molar proportion of copper, based on all metals present on the catalyst, is 0.75 to 1, and where the support comprises discrete particles of silicon dioxide or silicon carbide having an average diameter of 4.0 mm to 15 mm;

(II) optionally activating the hydrogenation catalyst by treating with hydrogen in the absence of the aromatic nitro compound; and (III) reacting the aromatic nitro compound with hydrogen in the presence of the optionally activated hydrogenation catalyst to obtain the aromatic amine, wherein the hydrogenation catalyst comprises a tetraamminecopper carbonate-based impregnated catalyst, and wherein the aromatic nitro compound is of the formula:

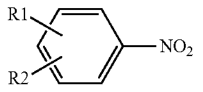

in which R1 and R2 are hydrogen.

2. The process as claimed in claim 1, in which step (II) is conducted and the treatment with hydrogen is effected at a temperature of 180° C. to 240° C.

3. The process as claimed in claim 1, in which step (III) is conducted:

adiabatically at a temperature of 160° C. to 500° C., or isothermally at a temperature of 180° C. to 550° C.

4. The process as claimed in claim 1, in which step (III) is conducted:

adiabatically at a molar ratio of hydrogen to nitro groups of 10 to 200, or isothermally at a molar ratio of hydrogen to nitro groups of 3 to 100.

5. The process as claimed in claim 1, in which the proportion by mass of copper compounds, calculated as metallic Cu, in the hydrogenation catalyst provided in (I), based on the total mass thereof, is 3% to 35%.

6. The process as claimed in claim 1, in which the hydrogenation catalyst used comprises a tetraamminecopper carbonate/ammonium carbonate-based impregnated catalyst or a tetraamminecopper carbonate/ammonium acetate-based impregnated catalyst.

7. The process as claimed in claim 1, in which step (I) comprises:

(a) dissolving a copper carbonate in aqueous ammonia to obtain an ammoniacal copper carbonate solution;

(b) impregnating the support with the ammoniacal copper carbonate solution obtained in (a), followed by drying of the impregnated support thus obtained to obtain a catalyst precursor, and (c) calcining the catalyst precursor obtained in (b) to form the tetraamminecopper-based impregnated catalyst.

8. The process as claimed in claim 7, in which the ammoniacal copper carbonate solution used for impregnation has a pH at 20° C. of 7.0 to 14.

9. The process as claimed in claim 7, in which the support in step (b) is impregnated with the ammoniacal copper carbonate solution obtained in (a) in such a way as not to exceed the maximum absorptivity of the support determined by means of saturation with water.

10. The process as claimed in claim 9, in which the maximum absorptivity of the support is undershot by not more than 5%.

11. The process as claimed in claim 9, in which the maximum absorptivity of the support is undershot by at least 2%.

12. The process as claimed in claim 10, in which the maximum absorptivity of the support is undershot by at least 2%.

13. The process as claimed in claim 1, in which the discrete particles are in the form of cylinders, aggregates of cylinders, or are of a spherical form, where the average diameter in the case of cylinders refers to a cylinder's base and in the case of aggregates of cylinders refers to a theoretical circle's diameter encircling the base of an aggregate of cylinders, where the length of a cylinder is greater than its diameter.

14. The process as claimed in claim 1, in which step (III) is conducted adiabatically at a temperature of 160° C. to 500° C.

15. The process as claimed in claim 1, in which step (III) is conducted adiabatically at a molar ratio of hydrogen to nitro groups of 10 to 200.

16. The process as claimed in claim 1, wherein the reacting is conducted in the gas phase and the optionally activated hydrogenation catalyst is disposed in a fixed catalyst bed.

* * * * *